United States Patent
Vyhmeister et al.

(10) Patent No.: US 10,660,633 B2
(45) Date of Patent: May 26, 2020

(54) SUTURE ANCHOR AND METHOD FOR ATTACHING SOFT TISSUE TO BONE

(71) Applicants: Edwin D. Vyhmeister, Soldotna, AK (US); Jeff A. Jensen, Marysville, WA (US)

(72) Inventors: Edwin D. Vyhmeister, Soldotna, AK (US); Jeff A. Jensen, Marysville, WA (US)

(73) Assignee: Edwin D. Vyhmeister, Soldotna, AK (US)

(*) Notice: Subject to any disclaimer, the term of this patent is extended or adjusted under 35 U.S.C. 154(b) by 450 days.

(21) Appl. No.: 13/829,430

(22) Filed: Mar. 14, 2013

(65) Prior Publication Data
US 2013/0274798 A1 Oct. 17, 2013

Related U.S. Application Data

(60) Provisional application No. 61/622,822, filed on Apr. 11, 2012.

(51) Int. Cl.
*A61B 17/04* (2006.01)

(52) U.S. Cl.
CPC .. *A61B 17/0401* (2013.01); *A61B 2017/0414* (2013.01); *A61B 2017/0437* (2013.01)

(58) Field of Classification Search
CPC ........ A61B 17/0401; A61B 2017/0437; A61B 2017/0414; A61B 2017/0427
See application file for complete search history.

(56) References Cited

U.S. PATENT DOCUMENTS

| | | | | |
|---|---|---|---|---|
| 4,961,743 A * | 10/1990 | Kees, Jr. | ............ | A61B 17/1227 606/151 |
| 5,733,307 A * | 3/1998 | Dinsdale | ............ | A61B 17/0401 606/104 |
| 6,997,189 B2 * | 2/2006 | Biggs | ............... | A61B 17/00234 128/898 |
| 2004/0249398 A1 * | 12/2004 | Ginn | ................... | A61B 17/0057 606/151 |
| 2009/0240266 A1 * | 9/2009 | Dennis | ............... | A61B 17/1227 606/151 |

* cited by examiner

*Primary Examiner* — Melanie R Tyson

(57) ABSTRACT

A suture anchor made of a single length of wire that forms a suture retaining loop having two diverging legs, each having a pointed end. The transverse spacing of the diverging legs is greater than the diameter of the bone tunnel. The suture anchor may be spring loaded and set into the bone tunnel so that the distal points of each diverging leg are below the surface of a bone cortex, the sharp distal points of each diverging leg expand out laterally under pressure and penetrate the bone tunnel wall prohibiting removal of the suture anchor. The diverging legs further penetrate the bone tunnel wall in response to applied withdrawal forces.

10 Claims, 2 Drawing Sheets

SUTURE ANCHOR AND METHOD FOR ATTACHING SOFT TISSUE TO BONE

REFERENCE TO RELATED APPLICATIONS

This application claims the priority of provisional application Ser. No. 61/622,822 filed Apr. 11, 2012; the disclosures of which is incorporated herein by reference.

BACKGROUND OF THE INVENTION

1. Technical Field

This invention pertains to the methods and apparatus utilized in surgical procedures involving the fixation of soft tissue to bone tissue and in particular to a novel method and apparatus for anchoring sutures to bone.

2. Discussion of the Prior Art

As a common procedure of various surgeries, open, arthroscopic or endoscopic, it is necessary to attach a suture to bone tissue. For example, in certain procedures requiring the suturing of soft tissue such as muscle, ligaments or tendons to bone tissue the suture must be attached to bone in order for the soft tissue to be sutured to the bone. Prior art includes numerous suture anchors in various sizes, types and methods which can be adapted to be secured to pre-drilled holes or tunnels in the bone and most of these anchors have one or more disadvantage.

Some prior art suture anchors require the anchor to be hammered into place or impacted by special tools to essentially drive or fix the anchor to the bone, as exemplified in U.S. Pat. No. 5,102,421 (Anspach, Jr.) and U.S. Pat. No. 5,141,520 (Gobal). This design has the disadvantage of potential trauma and damage to the bone and surrounding tissues. This type also has the possibility that it could come loose and it has limited applications due to the increased access that is required to apply the impacting forces to fix the anchor to the bone. Another disadvantage of this type of anchor is that it is only suited to larger bone because sometimes smaller bone and surrounding or attached tissues cannot handle the impact forces required to set this type of anchor into place. The hammered in type of anchor is also associated with high costs and increased difficulty removing them in the future if the need arises. Other disadvantages of this type of anchor is that special tools are also required to set them in place, they are time consuming to install and they require a larger hole or bone tunnel to be used which can weaken the bone.

Prior art also includes many screw in or threaded types of anchors that are mounted to a bone tunnel by twisting or screwing in the anchor so that its threads contact and grip the sides of the bone tunnel wall, as exemplified by U.S. Pat. No. 5,156,616 (Meadows) and U.S. Pat. No. 7,645,293 (Martinek et al.). The screw insertion method has disadvantages because it tends to be time consuming, very costly and typically requires specialized high priced tools to use. Another disadvantage of the screw in anchor is that many screw in designs require the bone tunnel hole to be larger and tapped to receive the screw in anchor. The larger hole, the tapping and or insertion of the screw can weaken the bone and cause additional damages to surrounding tissues and take more time to install. The screw in anchor design also has the disadvantage of being very high priced as compared to some other suture anchor designs.

Other suture anchor devices include designs that require extra holes to be drilled into the bone to accommodate special tools used to insert the anchor. Examples of this type of anchor include U.S. Pat. No. 4,741,330 (Hayhurst); U.S. Pat. No. 4,968,315 (Gatturna) and U.S. Pat. No. 4,899,743 (Nicholson). Drilling extra holes to accommodate the anchor or tools to install the anchor are disadvantages because the extra hole can weaken the bone and the installation process takes longer and is more complicated plus this style can have limited applications because of the need of the extra hole.

Many prior art anchors require special tools during the surgical installation procedure and without the specially designed installation tool the associated anchor could not be used or installed. These required tools have the disadvantage of being very expensive, intricate and highly specialized to one single task of inserting suture anchors only. Examples of this prior art include U.S. Pat. No. 8,137,383 (West, Jr. et al.) and U.S. Pat. No. 5,944,724 (Lizardi).

Other prior art of suture anchors include designs made of twisted wire but their engineering has strength disadvantaged due to their inherent design. None of the prior art showing anchors made from twisted wire are designed with legs that are straight by design. Although the prior art twisted wire designs can solve the problems of cost and simplicity associated with most other anchor designs, because the wire legs are bent they inherently offer less resistance to further bending than wires that are straight. When pressures are applied to the ends of a wire that is bent, it will bend easier than when pressures are applied to the ends of a straight wire. Prior art using twisted wire to fabricate a suture anchor has the disadvantage of the anchor pulling free from the bone tunnel because the legs bend easier and release their grip on the bone tunnel walls. Additionally, all prior art using bent wires have the disadvantage of the supporting legs on the same plane which also weakens the anchors holding ability as well. An example of this type of anchor include U.S. Pat. No. 5,501,696 (Trott).

Additionally, most of the foregoing exemplar prior art suture anchors suffer from the disadvantage of requiring special tools to insert and or deploy the anchor into the bone tunnel. These special tools add to the already high costs of suture anchors plus they complicate the insertion process and add time to the surgical procedure adding further to the high costs of using suture anchors for any surgery.

OBJECTS AND SUMMARY OF THE INVENTION

It is therefore an object of the present invention to provide improved methods and apparatus for anchoring suture to bone.

It is another object of the invention to provide a suture anchor that is suitable for use in various sizes, very, very small sizes as well as large sizes. The very small size would be suitable for use in small bone such as found in the fingers or toes and the larger size would be suitable for use in larger bones such as the leg.

A further object of the invention is to provide a suture anchor at significant cost savings. Cost savings would be realized through its simple design, minimal materials required for its construction, ease of manufacturing, ease of use and speed of installing and by producing the anchor from materials that have already been approved for use as implants by the FDA.

Another object of the invention is to provide a suture anchor that does not require any specially designed, specialized and dedicated tools to use.

It is yet another object of the invention to provide a suture anchor that is very quick and easy to use so that no special instructions are required.

It is another object of the invention to provide choices to the surgeon to use a suture anchor that is constructed out of radio-graphically compatible, and/or hypo-allergenic, low antigenicity and/or bio-absorbable materials depending on their needs.

Another object of the invention is to provide a method and apparatus for securing a suture to a bone tunnel without requiring the bone tunnel diameter to be larger than necessary to accommodate the anchor.

It is yet another object of the invention to provide a method and apparatus for securing a suture to a bone tunnel without the need to drill extra holes to accommodate tools or provide access during installation.

In accordance to the present invention, a suture anchor is configured by bending a wire into a loop formed at the center of the wire length. The loop represents the proximal end of the anchor. The wire is twisted a full 495 to 510 degrees to close the loop creating a suture retaining loop. The two wire ends extend generally distally along opposite transverse sides of the suture retaining loop at a diverging 30 to 45 degree to angle forming two straight legs. The tips of each leg are cut at a bias of 45 degree angles to itself to define sharp points at the outer transverse lateral side of each leg.

Also in accordance with the present invention, the helix has a tight pitch (i.e. tight longitudinal spacing between successive loops) which creates resilient spring forces on the legs in two directions adding strength to the anchors holding power.

Also in accordance to the present invention the distance between the distal points of the two straight legs is greater than the diameter of the helix coil suture retaining loop.

Also in accordance to the present invention the suture anchor can be configured using different materials for various purposes. The wire that is bent into the anchor can be comprised of titanium which offers a low chance of body rejection as well as distinct advantages when using radiographic equipment such as an MRI because of its low interference rate to the radio waves and magnetism. The anchor can also be configured out of standard surgical stainless steel or what is commonly referred to as "Kirschner-Wire". The anchor can also be configured using bio-absorbable materials when preferred. All of these materials are already approved by the FDA as surgical implants.

DESCRIPTION OF THE PREFERRED EMBODIMENTS

Figure 2:
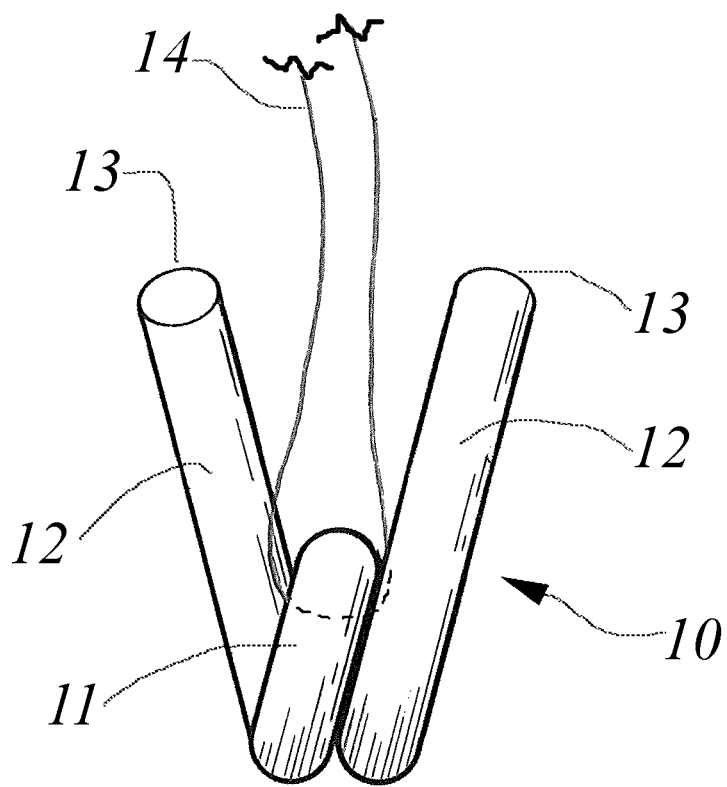
FIG. 2 is a side view of an anchor as shown in FIG. 1 and constructed in one embodiment of the present invention and showing a suture engaged and the tight pitch of the helix coil (i.e., tight longitudinal spacing between successive loops) and the resulting angles of the straight legs.
Figure 1:
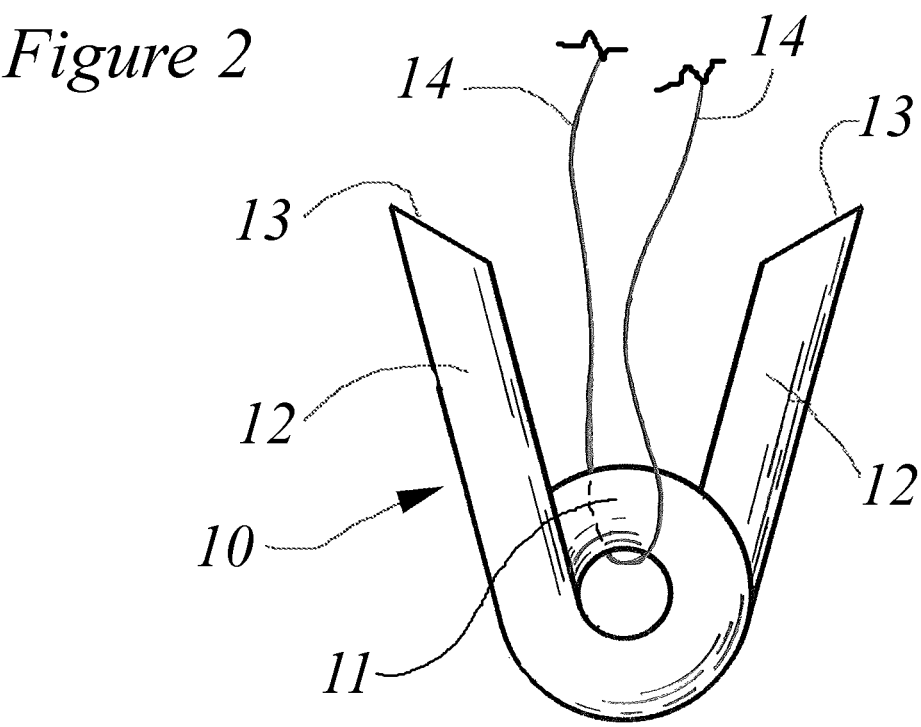
FIG. 1 is a view in plan of an anchor constructed in one embodiment of the present invention and showing a suture engaged through the helix shaped suture retaining loop.
Figure 3:
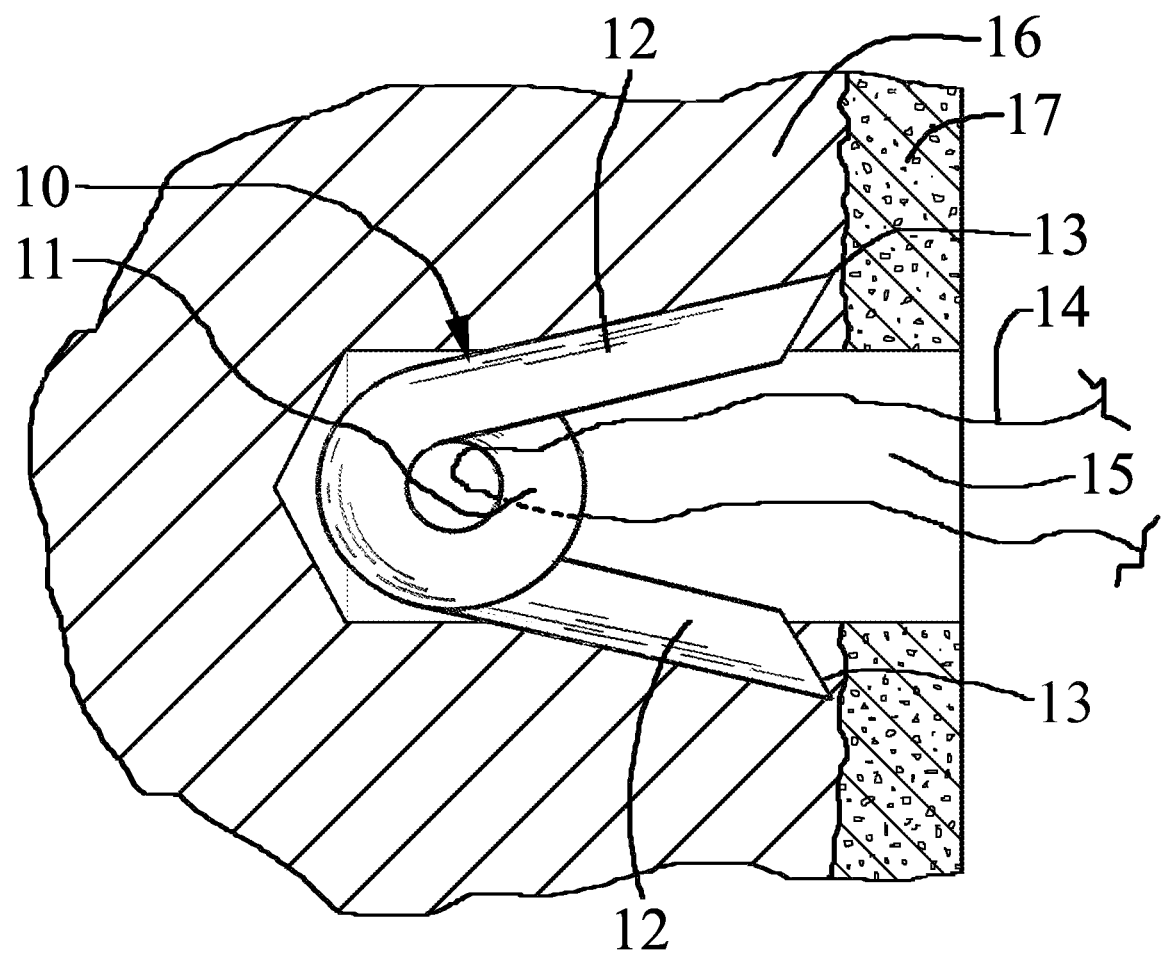
FIG. 3 is a plan view of an anchor fully inserted into a cross section of a bone tunnel and showing the distal points of the first and second legs engaged into the walls of the bone tunnel and the suture passing through the suture retaining loop of the anchor and extending to desired length out of the bone tunnel.

Referring specifically to FIGS. 1, 2 and 3, a resiliently flexible wire is bent and twisted to form a suture anchor 10 with a suture retaining loop 11 positioned at the center of a precisely measured and cut length of wire. The suture loop 11 constitutes the proximal end of the anchor device 10 and in the preferred embodiment has a helical shape that provides spring flexibility to the two wire ends that make up the two diverging legs 12. In the illustrated embodiment the wire forms approximately one and three quarters helical loops 11 with the ends of the wire extending away from the loop to make two legs 12 diverging at a desired angle of between 30 degrees to 45 degrees depending on the anchors intended use. The two legs 12, when unconstrained, have their pointed ends 13 spaced at a distance that is greater than the diameter of the bone tunnel 15 that has been drilled into the bone 16 to which the suture anchor is to be deployed. The suture 14 is passed through the suture retaining loop 11 prior to the anchors insertion into the predrilled bone tunnel 15. The anchor 10 is then inserted into the bone tunnel 15, suture retaining loop, distal end, first. The anchor 10 is inserted using common, readily available and popular surgical tools with no special tools being required. The two points 13 of the legs 12 define the anchors distal end and because the bone tunnel 15 has a diameter that is less than the distance between the proximal points 13, the legs 12 get compressed toward one another until the anchor 10 is inserted far enough into the bone tunnel 15 so that the legs 12 extend below the bone cortex 17 and protrude outward into the cancellous bone tunnel walls in opposite directions on an angular plane different from the helical coil plane.

The wire forming the anchor 10 must have sufficient rigidity, resiliency and resistance to bending to permit the anchors legs 12 and their proximal points 13 to penetrate the cancellous tissue surrounding the tunnel 15 below the bone cortex 17. It is important that the wire is resilient enough to be brought together close enough to enter the bone tunnel when the anchor is being inserted and with the helical coil offering enough spring to force the legs out into the walls of the bone tunnel and because of the tight spacing between the loops of the coil and the angles of the legs it is important to note that the outward spring forces that the helix applies to the legs is applied in two directions simultaneously.

It is also noted that any forceful pulling on the suture 14 will in effect increase the distance between the legs and increase the holding ability of the anchor. This is partly due to the 45 degree angle that the tips of the legs 13 are cut at as well as the double outward pressures applied by the helix coil.

What is claimed is:

1. A bone suture anchor for attaching a suture to a bone through insertion of the bone suture anchor into a predetermined bone tunnel diameter by resiliently compressing a first diverging leg and a second diverging leg by pushing the bone suture anchor into the predetermined bone tunnel, the suture anchor comprising:

at least one resiliently compressible suture retaining loop having a diameter substantially equal to the predetermined bone tunnel diameter, wherein
   the at least one resiliently compressible suture retaining loop is approximately one and three quarters loops;
the first diverging leg extending straight from the at least one resiliently compressible suture retaining loop to a first distal end, wherein
   the first distal end of the first diverging leg is pointed forming a first beveled cut,
     the first beveled cut angling laterally toward the at least one resiliently compressible suture retaining loop, and the first diverging leg occupying a first diverging leg plane defined along a length of the first diverging leg, the first diverging leg being resiliently compressible in the first diverging leg plane;

the second diverging leg extending straight from the at least one resiliently compressible suture retaining loop to a second distal end, wherein the second distal end of the second diverging leg is pointed forming a second beveled cut, the second beveled cut angling laterally toward the at least one resiliently compressible suture retaining loop, and the second diverging leg occupying a second diverging leg plane defined along a length of the second diverging leg, the second diverging leg being resiliently compressible in the second diverging leg plane;

the first diverging leg plane and the second diverging leg plane are different planes; and wherein an angle between the first diverging leg and the second diverging leg is from 30 to 45 degrees.

2. The bone suture anchor of claim 1, wherein
a distance between the first distal end of the first diverging leg and the second distal end of the second diverging leg is greater than the diameter of the predetermined bone tunnel.

3. The bone suture anchor of claim 1, wherein
the at least one resiliently compressible suture retaining loop has a tight pitch.

4. The bone suture anchor of claim 1, wherein
the suture anchor is made of a non-ferromagnetic metal.

5. The bone suture anchor of claim 4, wherein
the suture anchor is made of titanium.

6. The bone suture anchor of claim 1, wherein
the suture anchor is made of surgical steel.

7. The bone suture anchor of claim 1, wherein
the suture anchor is made of a bio-absorbable material.

8. The bone suture anchor of claim 1, wherein
the first beveled cut is 45 degrees, and the second beveled cut is 45 degrees.

9. The bone suture anchor of claim 1, wherein
the at least one resiliently compressible suture retaining loop is circular.

10. The bone suture anchor of claim 1, wherein
the first diverging leg and the second diverging leg extend vertically past the at least one resiliently compressible suture retaining loop when resiliently compressed.

* * * * *

UNITED STATES PATENT AND TRADEMARK OFFICE
CERTIFICATE OF CORRECTION

PATENT NO. : 10,660,633 B2  
APPLICATION NO. : 13/829430  
DATED : May 26, 2020  
INVENTOR(S) : Edwin D. Vyhmeister and Jeff A. Jensen Page 1 of 1

It is certified that error appears in the above-identified patent and that said Letters Patent is hereby corrected as shown below:

Assignee Name and Address:  
Wyhmeister, Edwin D. ,Soldotna ,AK

Please correct to:  
Vyhmeister, Edwin D., Soldotna, AK

Signed and Sealed this  
Sixteenth Day of June, 2020

Andrei Iancu  
*Director of the United States Patent and Trademark Office*